United States Patent
Lee et al.

(10) Patent No.: US 7,331,231 B2
(45) Date of Patent: Feb. 19, 2008

(54) APPARATUS AND METHOD FOR MEASURING MICRO MASS USING OSCILLATION CIRCUIT

(75) Inventors: Soo-suk Lee, Suwon-si (KR); Won-kyu Moon, Pohang-si (KR); Yeol-ho Lee, Pohang-si (KR)

(73) Assignee: Samsung Electronics Co., Ltd. (KR)

( * ) Notice: Subject to any disclaimer, the term of this patent is extended or adjusted under 35 U.S.C. 154(b) by 139 days.

(21) Appl. No.: 10/974,455

(22) Filed: Oct. 27, 2004

(65) Prior Publication Data
US 2005/0097962 A1 May 12, 2005

(30) Foreign Application Priority Data
Nov. 12, 2003 (KR) .................. 10-2003-0079898

(51) Int. Cl.
*G01N 29/02* (2006.01)
*G01N 31/00* (2006.01)

(52) U.S. Cl. .............. 73/579; 73/24.01; 73/24.06; 422/88; 422/68.1

(58) Field of Classification Search .............. None
See application file for complete search history.

(56) References Cited

U.S. PATENT DOCUMENTS

| 4,623,030 | A | | 11/1986 | Portman, Jr. et al. ....... 177/210 |
| 5,719,324 | A | | 2/1998 | Thundat et al. ............ 73/24.01 |
| 6,126,311 | A | * | 10/2000 | Schuh ......................... 374/21 |
| 6,972,423 | B2 | * | 12/2005 | Welland et al. ............. 250/573 |
| 2003/0011389 | A1 | | 1/2003 | Nakayama et al. ......... 324/727 |
| 2003/0032293 | A1 | * | 2/2003 | Kim et al. ................... 438/694 |
| 2003/0127944 | A1 | | 7/2003 | Clark et al. ............. 310/316.01 |
| 2003/0166039 | A1 | * | 9/2003 | Hubler et al. ................. 435/34 |
| 2003/0209058 | A1 | * | 11/2003 | Merrill ....................... 73/53.01 |
| 2004/0208788 | A1 | * | 10/2004 | Colton ....................... 422/68.1 |
| 2005/0009197 | A1 | * | 1/2005 | Adams et al. .............. 436/164 |

FOREIGN PATENT DOCUMENTS

| EP | 0 072 744 | 2/1983 |
| JP | 2001056278 | 2/2001 |
| JP | 2002517745 | 6/2002 |
| JP | 2002350218 | 12/2002 |
| JP | 2002543403 | 12/2002 |
| KR | P2003-0016244 | 2/2003 |

OTHER PUBLICATIONS

European Search Report ; Application No. EP 04 02 6084.6-2213; Dated Feb. 1, 2005.
Office Action issued by the Chinese Patent Office dated Jul. 28, 2006 for Application No. 200410094659.4 (All references in Office Action are cited above.).
Japanese Office Action for Application No. 2004-311053 dated Jul. 31, 2007, No Translation provided.

* cited by examiner

*Primary Examiner*—Hezron Williams
*Assistant Examiner*—Rose M Miller
(74) *Attorney, Agent, or Firm*—Cantor Colburn LLP

(57) ABSTRACT

A micro mass measuring apparatus includes a cantilever on which a subject is attached, a piezoelectric element formed on the cantilever, an oscillation circuit for actively vibrating the cantilever and providing a varied resonance frequency by the subject, and a frequency measuring device for measuring a resonance frequency of the cantilever.

13 Claims, 8 Drawing Sheets

APPARATUS AND METHOD FOR MEASURING MICRO MASS USING OSCILLATION CIRCUIT

This application claims the priority of Korean Patent Application No. 2003-79898, filed on Nov. 12, 2003, in the Korean Intellectual Property Office, the disclosure of which is incorporated herein in its entirety by reference.

BACKGROUND OF THE INVENTION

1. Field of the Invention

The present invention relates to an apparatus and method for measuring micro mass using an oscillation circuit, and more particularly, to an apparatus and method for measuring mass of biomolecule such as DNA and protein by oscillating a cantilever using an oscillation circuit.

2. Description of the Related Art

In a mass micro-balancing technology, variation of a resonance frequency of a micro matter according to a variation of mass is first measured, and the varied mass is measured based on the varied resonance frequency.

A typical method for measuring micro matter using such a mass micro-balancing technology is a quartz crystal mass micro-balancing (QCM). Sauerbrey systematically theorizes a relationship between variation of resonance frequency and increase of mass in the QCM. According to the theory of Sauerbrey, the resonance frequency is linearly reduced as the mass is increased.

The QCM is generally used to measure mass per unit area of a subject (to-be-measured). The QCM determines increased mass according to variation of a shear mode of quartz oscillator. The QCM has advantages that it is designed to make it easy to input/output a signal and excel in sensitiveness. However, the mass must be evenly distributed on a surface of the quartz oscillator and a shear mode having a high resonance frequency must be used.

As the mass micro-balancing technology, a method using light and a method using piezo-resistance have been proposed.

U.S. Pat. No. 5,719,324 discloses a sensor for measuring micro mass using light.

As shown in FIG. 1, the sensor disclosed in the Patent comprises a cantilever 12, a piezoelectric element 10 supporting the cantilever 12, and a laser diode 19 formed on a tip portion of the cantilever 12 to eradiate laser beams 20. The piezoelectric element 10 is excited by a pulse wave from an oscillator 14, thereby exciting the piezoelectric element 10.

When the subject is disposed on the cantilever 12, the cantilever 12 is deformed by the mass of the examining subject. As this point, the laser beams 20 eradiated from the cantilever 12 are detected by a photodetector 27 having first and second cells 23 and 29. The deformation of the cantilever 12 is measured based on an amount of light detected by the photodetector 27, thereby determining varied mass. The reference numerals 30 and 34 indicate counting circuits, the reference numerals 36 and 37 represent differential circuits, and the reference numerals 38 and 39 indicate signals outputted from the differential circuits 36 and 37.

However, the method using the light requires an accurate position control of the laser diode and the photodetector. Therefore, a separated position controller controlling the position of the laser diode and the photodetector is required. In addition, since a member for oscillating the cantilever and a member for measuring mass are formed independent from each other, a volume of the apparatus is increased, complicating the structure.

In the method using the piezo resistance, a piezo resistance material is doped in the cantilever to increase the mass of the cantilever, causing the cantilever to be deformed by the increased mass. The deformation of the cantilever causes the resistance to be varied. The mass is measured by measuring output voltage varied by the resistance variation.

However, in the above-described methods, since the cantilever is not actively oscillated, the variation of the cantilever is too small to precisely measure micro mass. Furthermore, a variety of periphery devices such as a device for measuring varied resistance, a device for comparing an input signal for oscillating with an output signal of a resonance frequency varied by the increased mass, and the like are required, increasing the manufacturing costs and volume of the apparatus.

SUMMARY OF THE INVENTION

The present invention provides an apparatus and method that can precisely measure micro mass of a subject without using any additional periphery devices by actively self-vibrating a cantilever using an oscillation circuit.

In an aspect of the present invention, there is provided a micro mass measuring apparatus comprising a cantilever on which a subject is attached; a piezoelectric element formed on the cantilever; an oscillation circuit for actively vibrating the cantilever and providing a varied resonance frequency by the subject; and a frequency measuring device for measuring a resonance frequency of the cantilever.

According to an embodiment of the present invention, the oscillation circuit comprises an amplifier for amplifying an output signal from the cantilever; and a feedback for inputting the amplified signal to the cantilever.

A shape ratio of the cantilever may be determined by sensitiveness and a separation factor.

The separation factor may be defined by a value obtained by dividing a difference between a first resonance frequency of the cantilever and a second resonance frequency varied by the subject by the first resonance frequency.

The cantilever may be formed in a triangular-shape.

A ratio between a length, width and thickness of the cantilever may be in a range of 20:6:1-20:18:1.

An area of the cantilever, on which the subject is attached, may be $1/15$-$1/10$ of an entire area of the cantilever.

A thickness of the piezoelectric element may be about 40-60% of a thickness of the cantilever. A length of the piezoelectric element may be about 50-60% of a length of the cantilever.

In another aspect of the present invention, there is provided a method for measuring micro mass using a mass micro-balancing technology, comprising self-vibrating a cantilever through a piezoelectric element using an oscillation circuit at a first resonance frequency; attaching a subject on the cantilever and self-vibrating the cantilever with a second resonance frequency varied by the subject; and measuring mass of the subject using a difference between the first and second resonance frequencies.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
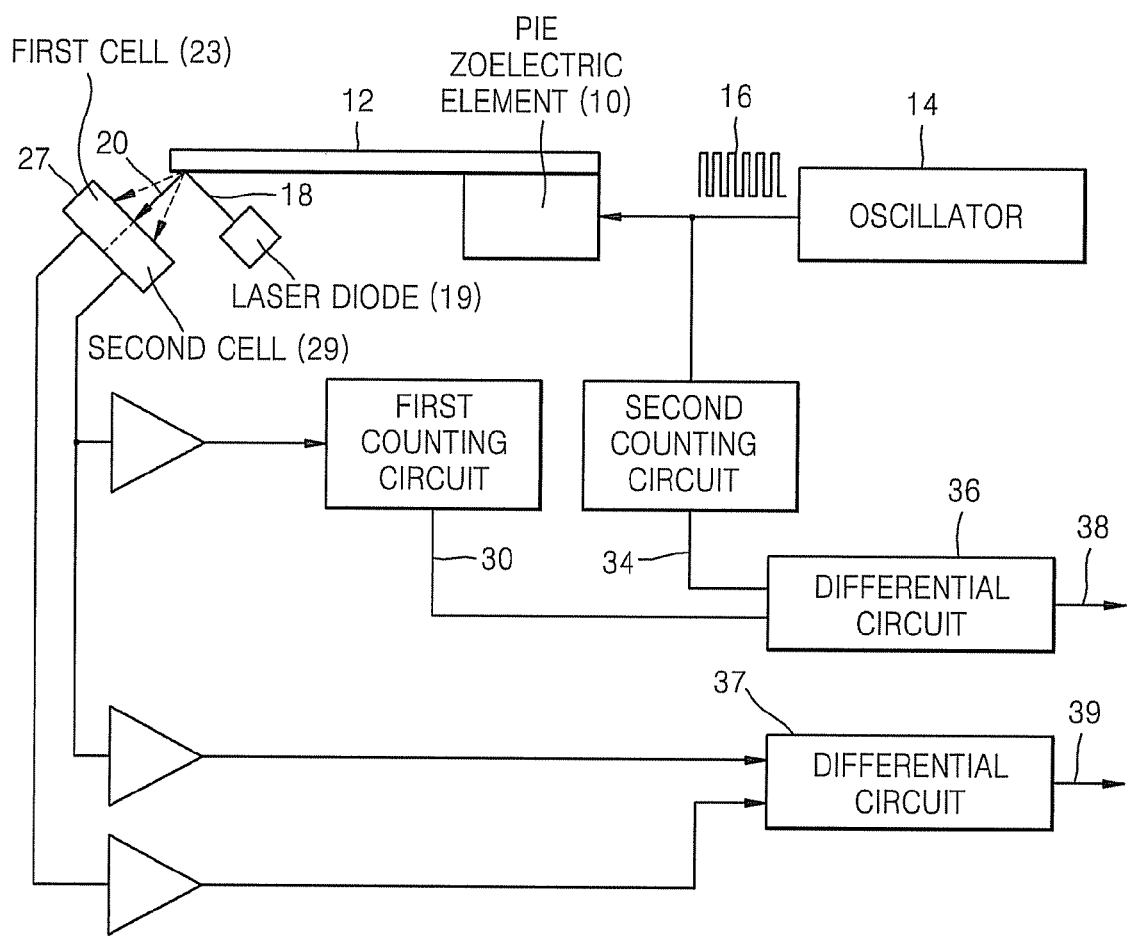
FIG. 1 is a schematic diagram of a conventional micro cantilever sensor.

The present invention will now be described more fully with reference to the accompanying drawings, in which exemplary embodiments of the invention are shown. The invention may, however, be embodied in many different forms and should not be construed as being limited to the embodiments set forth herein; rather, these embodiments are provided so that this disclosure will be thorough and complete, and will fully convey the concept of the invention to those skilled in the art. In the drawings, the thicknesses of layers and regions are exaggerated for clarity.

Figure 2:
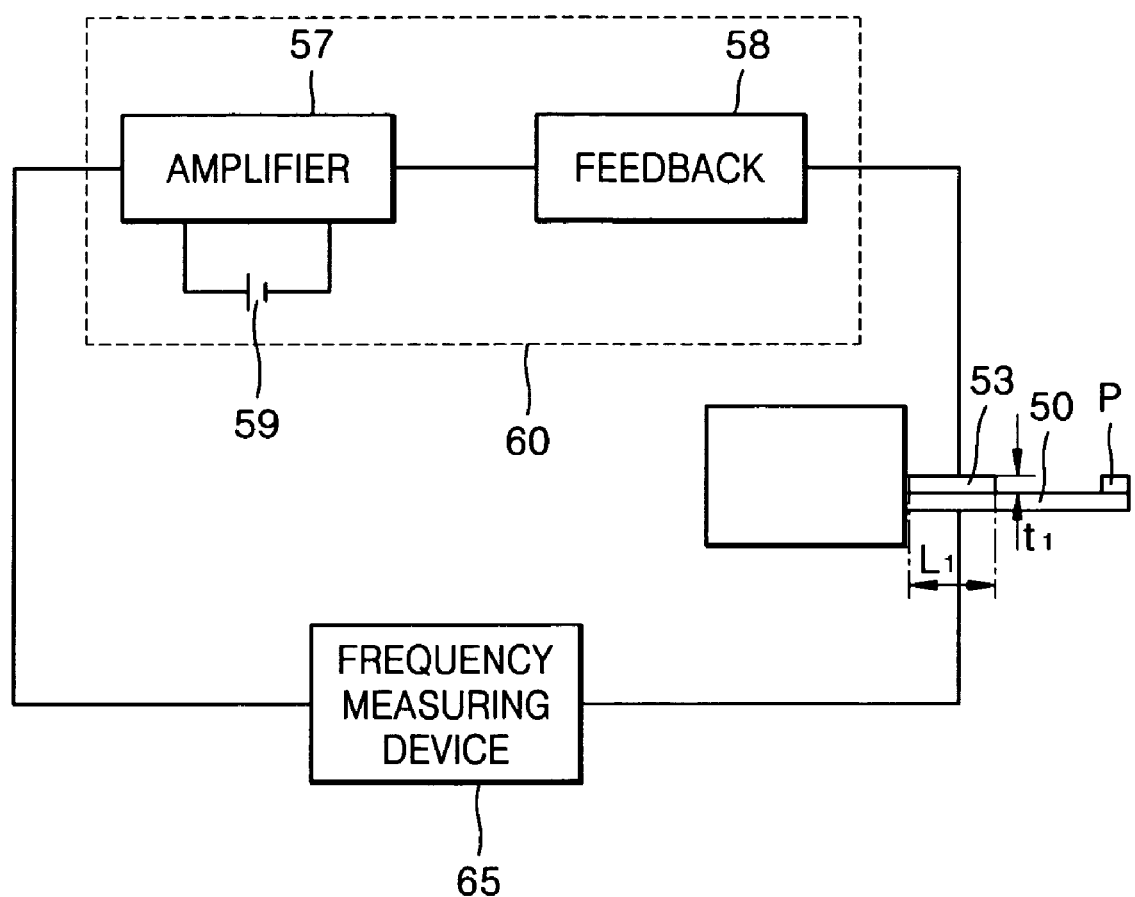
FIG. 2 is a schematic diagram of a micro mass measuring apparatus according to an embodiment of the present invention.

FIG. 2 shows a schematic diagram of a micro mass measuring apparatus according to an embodiment of the present invention.

Referring to FIG. 2, a micro mass measuring apparatus of the present invention comprises a micro cantilever 50 for measuring mass of a subject p and an oscillation circuit 60 for oscillating the micro cantilever 50 actively and for measuring a varied resonance frequency of the micro cantilever 50.

The subject can be biomolecle such as DNA and protein.

A piezoelectric element 53 is formed on the cantilever 50. The oscillation circuit 60 is coupled to the piezoelectric element 53. The piezoelectric element 53 may be formed by depositing PZT on the cantilever 50.

The oscillation circuit 60 comprises an amplifier 57 and a feedback 58. The amplifier 57 amplifies a first resonance frequency outputted from the piezoelectric element 53 of the micro cantilever 50 and the feedback 58 allows the piezoelectric element 53 to vibrate the cantilever 50 with the first resonance frequency.

A frequency measuring device 65 is coupled to the oscillation circuit 60 to measure a variation of the resonance frequency. The frequency measuring device 65 may be formed of a simple electric circuit using, for example, a pulse counter. When the frequency measuring device is coupled to the oscillation circuit 60, a micro variation of the resonance frequency, which is caused by the increase of mass when the subject p is disposed on the cantilever 50, can be easily measured.

As described above, by applying the oscillation circuit 60 to the micro cantilever 50 to which the piezoelectric element 53 is coupled, the cantilever 50 can continuously vibrate with the first resonance frequency. After the subject p is disposed on the micro cantilever 50, the resonance frequency varied by the subject p is measured by the frequency measuring device 65. Therefore, it is possible to vibrate itself and measure mass of the cantilever 50 using the single piezoelectric element 53.

The measuring apparatus of the present invention further comprises a data transferring device (not shown) for transferring the variation amount of the frequency to a computer.

To measure micro mass of the subject such as DNA and protein according to the present invention, the bio subject p is attached on an end of the micro cantilever 50 employing the oscillation circuit 60 and the micro mass of the bio subject p is measured using the mass micro-balancing technology.

The micro cantilever 50 deposited with the piezoelectric element 53 may be manufactured through a micro electro mechanical system (MEMS) process. The attachment of the bio subject p may be realized through a biochemical reaction.

The oscillation circuit 60 is comprised of the amplifier 57 for amplifying a signal from the cantilever 50 and the feedback 58 for inputting the amplified signal to the cantilever 50. There is further provided an electric power source 59 for supplying voltage to the oscillation circuit 60. The electric power source may be one of pulse and step-type power sources. A small battery may be used as the power source 59.

Since the micro cantilever 50 is a simple mechanical structure which clearly show displacement and formed in a micro-size through the MEMS process, it can be applied to a lab-on-a-chip (LOC) that can measure micro mass of a bio subject such as the DNA and protein.

The micro cantilever 50 is preferably designed having a shape and size that can provide sensitiveness that is good for measuring the micro mass. For example, when mass density of the DNA or protein is 10-15 g/μm2, it is preferable that the cantilever 50 is designed having a shape and size providing a sensitiveness of about 1 Hz/10-15 g and resolution of about 10-15 g/Hz.

That is, it is preferable that the cantilever is designed having a simple shape and a size that can provide sensitiveness required for the measurement of the micro mass. When the cantilever has a simple shape, the MEMS process can be simplified.

Figure 3A:
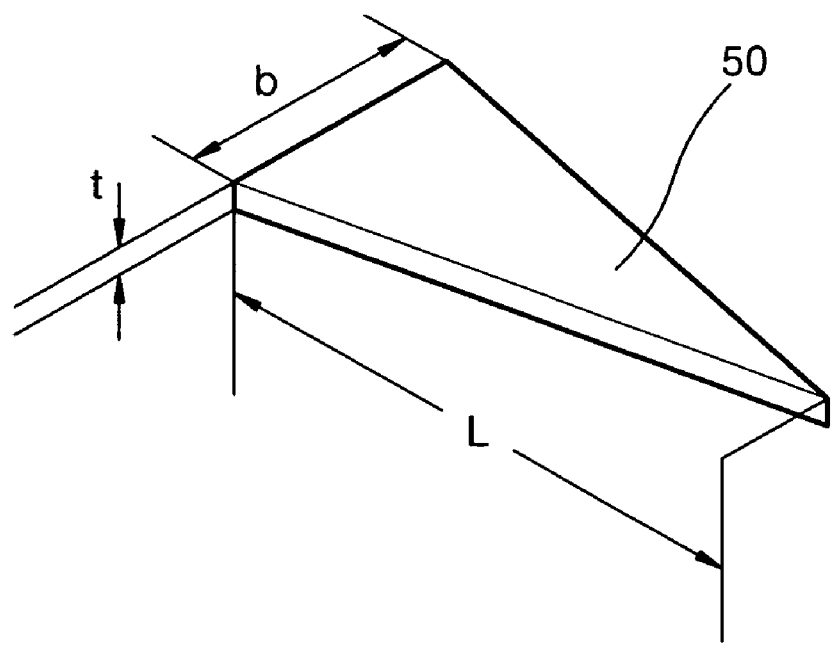
FIGS. 3A and 3B are views illustrating examples of a cantilever employed to a micro mass measuring apparatus according to an embodiment of the present invention.
Figure 3B:
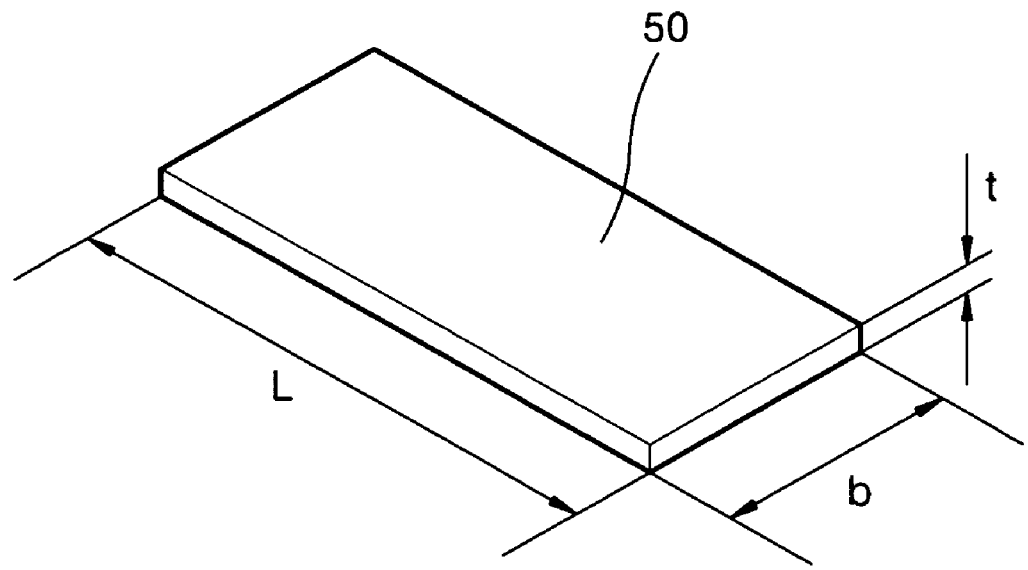

Furthermore, it is preferable that the micro cantilever 50 is designed having a shape and size that can satisfy a separation factor proper to measure the micro mass. The cantilever 50 can be designed satisfying both the sensitiveness and the separation factor. For example, as shown in FIGS. 3a and 3b, the cantilever 50 may be designed having a triangular-shape or a rectangular-shape. The sensitiveness and separation factor of the triangular cantilever will be compared with those of the rectangular cantilever.

When the subject p is not attached on the micro cantilever 50, a resonance frequency fr of the rectangular cantilever is as follows:

$$f_r = \frac{1}{2\pi}\sqrt{\frac{k_r}{0.24m_r}} \qquad \text{[Formula 1]}$$

where, kr and mr are respectively stiffness and mass of the rectangular cantilever.

When the subject p is not attached on the micro cantilever 50, a resonance frequency ft of the triangular cantilever is as follows:

$$f_t = \frac{1}{2\pi}\sqrt{\frac{k_t}{0.07m_t}} \qquad \text{[Formula 2]}$$

where, kt and mt are respectively stiffness and mass of the triangular cantilever.

When the subject p is attached on the micro cantilever 50, a varied resonance frequency f0r of the rectangular cantilever is as follows:

$$f_{0_r} = \frac{1}{2\pi}\sqrt{\frac{k_r}{\Delta m + 0.24m_r}} \qquad \text{[Formula 3]}$$

When the subject p is attached on the micro cantilever 50, a varied resonance frequency f0t of the triangular cantilever is as follows:

$$f_{0_t} = \frac{1}{2\pi}\sqrt{\frac{k_t}{\Delta m + 0.07m_t}} \qquad \text{[Formula 4]}$$

When the cantilever is formed in the rectangular-shape, a variation $\Delta$fr of the resonance frequency according to the variation of the micro mass of the subject p can be calculated using Formulas 1 and 3. That is, the variation $\Delta$fr of the resonance frequency is as follows:

$$\Delta f_r = \frac{1}{2\pi}\sqrt{\frac{k_r}{0.24m_r}}\left(1 - \frac{1}{\sqrt{1 + \Delta m/0.24m_r}}\right) \qquad \text{[Formula 5]}$$

When the cantilever is formed in the triangular-shape, a variation $\Delta$ft of the resonance frequency according to the variation of the micro mass of the subject p can be calculated using the Formulas 2 and 4. That is, the variation $\Delta$ft of the resonance frequency is as follows:

$$\Delta f_t = \frac{1}{2\pi}\sqrt{\frac{1}{0.07m_t}}\left(1 - \frac{1}{\sqrt{1 + \Delta m/0.07m_t}}\right) \qquad \text{[Formula 6]}$$

Here, since mass mr and mt of the cantilever is sufficiently greater than mass $\Delta$m of the subject p, when an assumption ($\Delta$m/m<<1) is applied to Formulas 5 and 6, $\Delta$fr and $\Delta$ft are obtained by following Formulas 7 and 8 defined by Taylor's expansion.

$$\Delta f_r \approx \frac{1}{2\pi}\sqrt{\frac{k_r}{0.24m_r}}\left(\frac{1}{2}\right)\left(\frac{\Delta m}{0.24m_r}\right) \qquad \text{[Formula 7]}$$

$$\Delta f_t \approx \frac{1}{2\pi}\sqrt{\frac{k_t}{0.07m_t}}\left(\frac{1}{2}\right)\left(\frac{\Delta m}{0.07m_t}\right) \qquad \text{[Formula 8]}$$

According to Formulas 1, 2, 7 and 8, the relationship between the resonance frequency variation $\Delta$f by the mass variation A m caused by the subject p and the mass and resonance frequency of the cantilever can be represented by the following Formula 9.

$$\frac{\Delta m}{\Delta f} \propto \frac{m}{f} \qquad \text{[Formula 9]}$$

In Formula 9, $\Delta$m/$\Delta$f(g/Hz) represents resolution. The sensitiveness is an inverse number of the resolution. That is, the lower the resolution, the higher the sensitiveness. That is, when the resonance frequency per unit mass is greatly varied, it means that the sensitiveness is high.

In addition, the resolution of the micro cantilever is proportional to its m/f, and the sensitiveness thereof is proportional to the f/m. Accordingly, a cantilever that is designed having small mass and a high resonance frequency is more proper for the micro mass measuring apparatus.

As shown in FIGS. 3A and 3B, the sensitiveness of the cantilever formed in the triangular-shape will be compared with that of the cantilever formed in the rectangular-shape with regards to a length L, a width b and a thickness t of the cantilever 50. At this point, it is assumed that the triangular cantilever and the rectangular cantilever are formed in an identical material and have same a length, same a width and same a thickenss.

The stiffness Kr of the rectangular cantilever and the stiffness Kt of the triangular cantilever can be respectively represented by following Formulas 10 and 11. Here, E, I, $\rho$ are respectively the modulus coefficient, second moment of inertia of area, density of the cantilever.

$$k_r = \frac{3EI}{L^3} = \left(\frac{E}{4}\right)\left(\frac{bt^3}{L^3}\right) \qquad \text{[Formula 10]}$$

$$k_t = \left(\frac{E}{6}\right)\left(\frac{bt^3}{L^3}\right) \qquad \text{[Formula 11]}$$

The mass mr of the rectangular cantilever and the mass mt of the triangular cantilever are as follows:

$$m_r = \rho bLt \qquad \text{[Formula 12]}$$

$$m_t = \frac{1}{2}\rho bLt \qquad \text{[Formula 13]}$$

When Formulas 10 and 12 are applied to Formula 7, Formula 14 can be obtained as follows:

$$\left(\frac{\Delta f}{\Delta m}\right)_r \approx 2.1 \left(\frac{1}{2\pi}\right)\left(\frac{E^{1/2}}{\rho^{3/2}}\right)\left(\frac{1}{bL^3}\right) \quad \text{[Formula 14]}$$

When Formulas 11 and 13 are applied to Formula 7, Formula 15 can be obtained as follows:

$$\left(\frac{\Delta f}{\Delta m}\right)_t \approx 30 \left(\frac{1}{2\pi}\right)\left(\frac{E^{1/2}}{\rho^{3/2}}\right)\left(\frac{1}{bL^3}\right) \quad \text{[Formula 15]}$$

When comparing Formula 14 with Formula 15, it can be noted that the sensitiveness $(\Delta f/\Delta m)_t$ of the triangular cantilever is relatively higher than that $(\Delta f/\Delta m)_r$ of the rectangular cantilever. This notes that it is preferable that the cantilever is formed in the triangular-shape. However, as far as the sensitiveness and the separation factor are satisfied, the rectangular cantilever can be also used.

Figure 4:
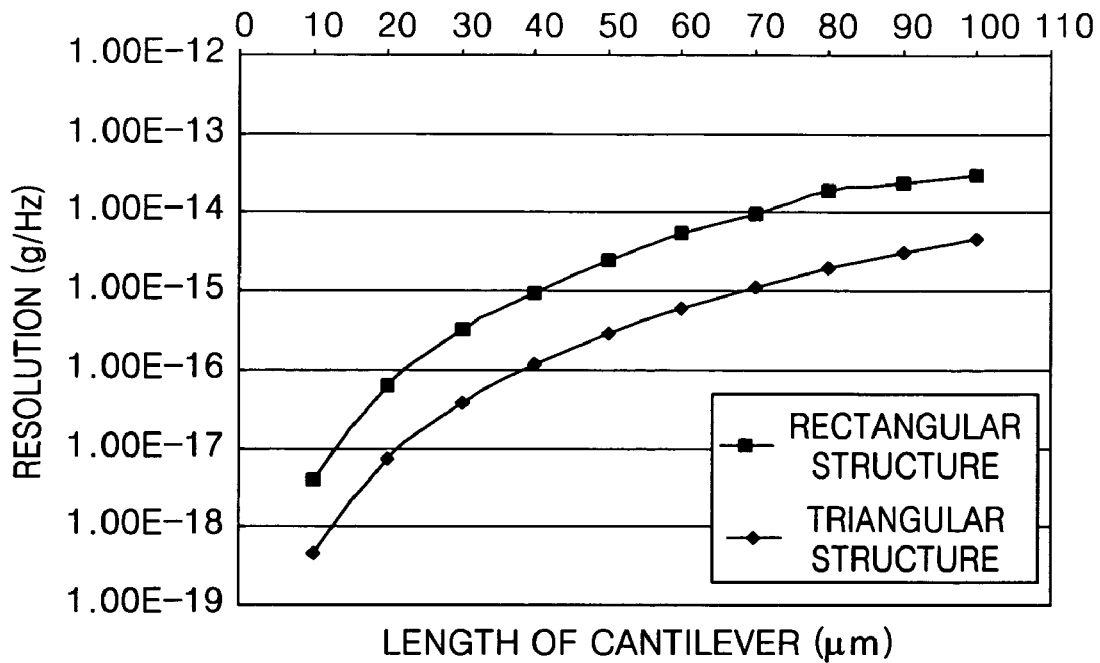
FIG. 4 is a graph illustrating resolution with respect to a length of a cantilever employed to a micro mass measuring apparatus according to an embodiment of the present invention.

FIG. 4 shows a graph illustrating the resolutions of the triangular cantilever and the rectangular cantilever. The resolution is an inverse number of the sensitiveness. That is, the lower the resolution, the higher the sensitiveness.

Referring to FIG. 4, when a length L of the triangular cantilever is identical to that of the rectangular cantilever, the sensitiveness of the triangular cantilever is higher than that of the rectangular cantilever.

To determine an actual size of the triangular cantilever, a separation factor is first defined and a ratio between a length, width and a thickness of the cantilever is determined. Here, the separation factor is defined by a value obtained by dividing a difference between the first and second resonance frequencies of the cantilever by the first resonance frequency. The separation factor represents an adjacent degree of the first and second resonance frequencies.

A first resonance frequency mode is used for the cantilever used as a detecting sensor for detecting vibration of a series of structures where the infinity number of vibration modes are compositely generated. At this point, when the second resonance frequency is too near the first resonance frequency, it may be confused to measure the first resonance frequency. Accordingly, to accurately measure the first resonance frequency, an interval between the first and second resonance frequency must be above a predetermined level. The separation factor is defined to provide the predetermined level. Since the separation factor is defined by a value obtained by dividing the difference between the first and second resonance frequencies ft1 and ft2 of the triangular cantilever by the first resonance frequency ft1, it can be represented by Formula 16 as follows:

$$\frac{f_{t2} - f_{t1}}{f_{t1}} \quad \text{[Formula 16]}$$

The shape of the triangular cantilever is concretely determined by a shape ratio between a length, a width and a thickness. The shape ratio is determined to obtain a predetermined satisfactory value of the separation factor and a predetermined satisfactory value of the sensitiveness. The separation factor of the triangular cantilever will be described hereinafter.

Figure 5:
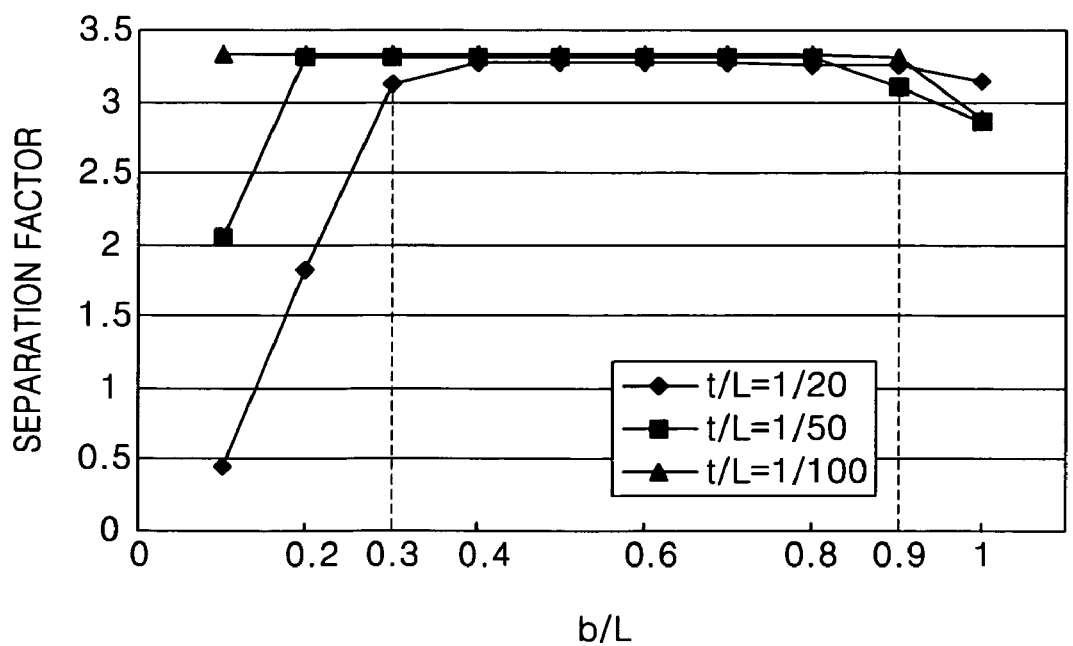
FIG. 5 is a graph illustrating a separation factor with respect to a ratio between a length and width of a cantilever employed to a micro mass measuring apparatus according to an embodiment of the present invention.

FIG. 5 shows a graph illustrating a separation factor of a triangular cantilever. The horizontal axis indicates a value (b/L) obtained by dividing a width b by a length L, and the vertical axis indicates a separation factor according to the variation of the value (b/L). In addition, results obtained when a ratio t/L of the length L to the thickness t is 1/20, 1/50 and 1/100 are illustrated.

Furthermore, when Formulas 11 and 13 are applied to Formula 2, a resonance frequency ft can be obtained as follows:

$$f_t = \frac{1}{2\pi}\sqrt{\frac{E}{3\rho}}\left(\frac{t}{L^2}\right) \quad \text{[Formula 17]}$$

Since the micro cantilever is operated in liquid to detect the bio subject, a mass added effect must be considered. That is, when the cantilever vibrates in the liquid, an effect is obtained as if the mass of the cantilever is increased due to the mass of the liquid. When the mass of the cantilever is increased, the resonance frequency of the cantilever is reduced. According to Formula 15, the sensitiveness of the cantilever is reduced as the resonance frequency is reduced.

By increasing a ratio (t/L) of the thickness to the length of the cantilever to increase the stiffness of the cantilever, it is possible to overcome the mass added effect. Therefore, it is most preferable to set the ratio (t/L) of 1/20.

Referring to FIG. 5, there is a range in which the separation factor has a predetermined value (a maximum value) regardless of the value (t/L). That is, the separation factor may be maximized when the ratio (b/L) is in a range of 0.3-0.9.

That is, when the value (t/L) is 1/20 and the value (b/L) is in a range of 0.3-0.9, the separation factor and the sensitiveness are simultaneously satisfied. Therefore, the shape ratio of the cantilever may be determined in a range of L:b:t=(20:6:1)–(20:18:1).

On the basis of the above-described shape ratio, the actual length L, width b and thickness t are determined.

Figure 8:
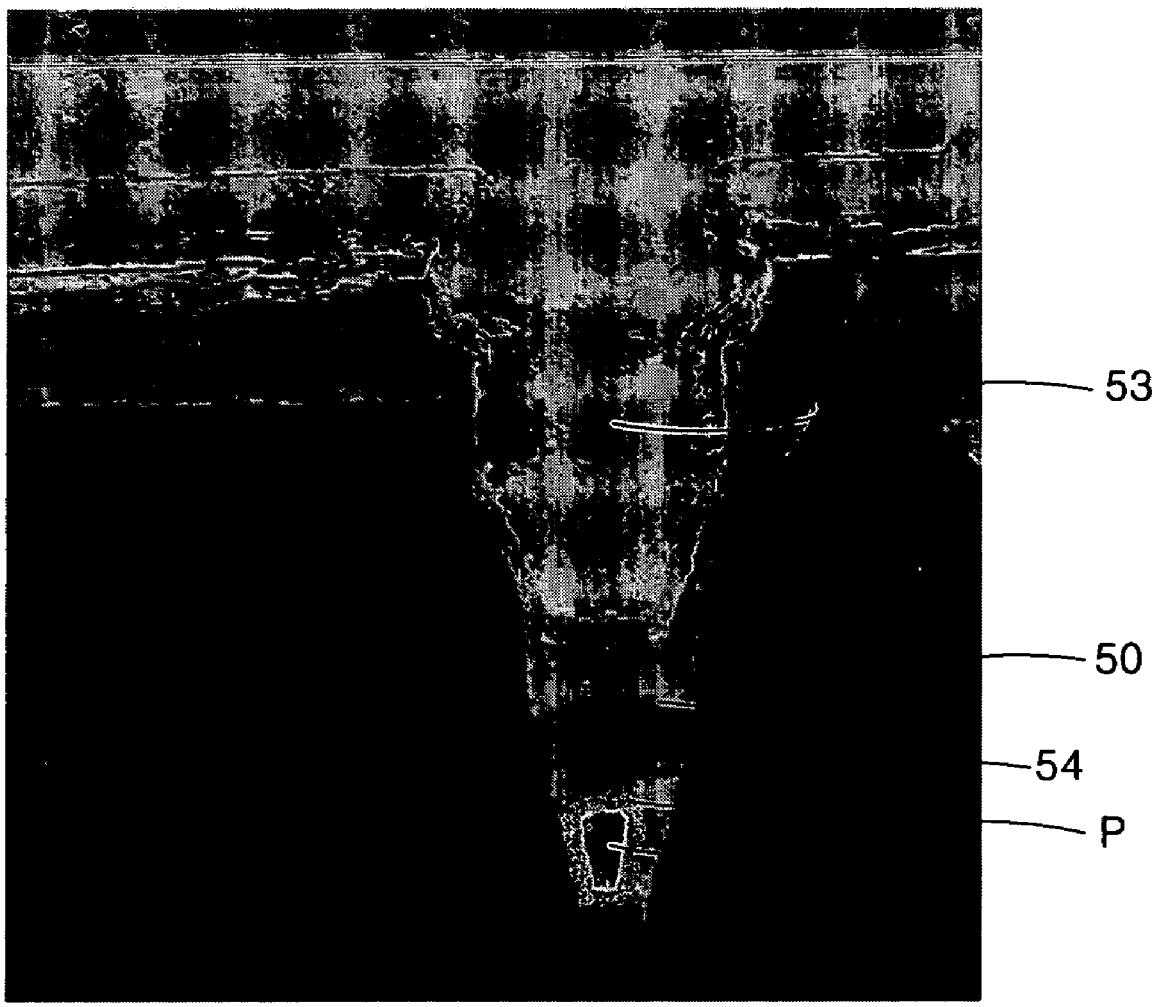
FIG. 8 is a photograph of a cantilever deposited with a piezoelectric element that is fabricated by an MEMS process.

FIG. 8 shows a photograph illustrating the micro cantilever manufactured through the MEMS process.

Referring to FIG. 8, a probe 54 is provided on an end of the cantilever 50. The bio subject such as DNA and protein is disposed on the probe 54. Since the bio subject p is disposed on an extreme end of the cantilever 54, the mass added effect can be maximized. An area of the probe 54 may be 1/10 of an entire area of the cantilever.

The bio subject is attached on the probe 54 through a biochemical reaction. That is, by concentrically attaching the bio subject on the extreme end of the cantilever as far as possible, the mass added effect can be maximized.

EXAMPLE

DNA has mass density of about 6×10−15 g/μm² and protein has mass density of about 2×10−15 g/μm². By applying these values to Formula 15 representing the sensitiveness, it is possible to measure the mass of the cantilever. When it is assumed that the area of the probe 54 is 1/10 of the that of the cantilever, the probe can be represented as "(1/10) (bL/2)=(1/10) (3L/10) L/2=3L²/200."

The cantilever is formed of silicon through the MEMS process. The silicon has property values (E=112 GPa, ρ=2330 kg/m3). When these property values are applied to Formula 15, the length L, width b and thickness b of the triangular cantilever can be determined.

At this point, it is assumed that the variation Δft of the resonance frequency is 150 Hz considering that the resonance frequency is varied within a range of 0-150 Hz as the bio subject p is locally attached on the cantilever. By measuring the resonance frequency, it is possible to determine mass of the bio subject p attached on the probe 54. The range of the resonance frequency is determined to suggest a determining reference if there is a specific bio subject that is a part of a lab on a chip (LOC) to which the inventive apparatus is applied. The probe 54 is biochemically-treated so that the bio-subject can be attached only on the probe 54. Therefore, the mass of the bio subject attached on the probe can be identified according to the variation of the resonance frequency.

For example, when the variation of the resonance frequency is 50 Hz, it can be regarded that the bio subject is attached on a ⅓ of the probe area. In addition, when the variation of the resonance frequency is 75 Hz, it can be regarded that the bio subject is attached on half of the probe area. The variation of 0-150 Hz of the resonance frequency is enough high when it is considered that the variation of the first resonance frequency according to the increase of the mass of the DNA or protein is very small.

The size of the triangular cantilever can be calculated based on the above-described conditions. When the bio subject is the DNA, the length, width and thickness of the cantilever are respectively 40 μm, 12 μm and 2 μm. When the bio subject is the protein, the length, width and thickness of the cantilever are respectively 100 μm, 30 μm and 5 μm. These values are determined through a numeral analysis considering area density of the DNA and protein with respect to cantilevers having an identical shape ratio to each other such that the cantilever can be manufactured through the MEMS process and have sufficient sensitiveness.

Next, a thickness and length of the piezoelectric element are determined. The piezoelectric element may be formed of the PZT. The size of the piezoelectric element may be determined to obtain a large mount of output current. When there is a large amount of output current, the mass detecting performance with respect to the subject p may be improved.

Figure 6:
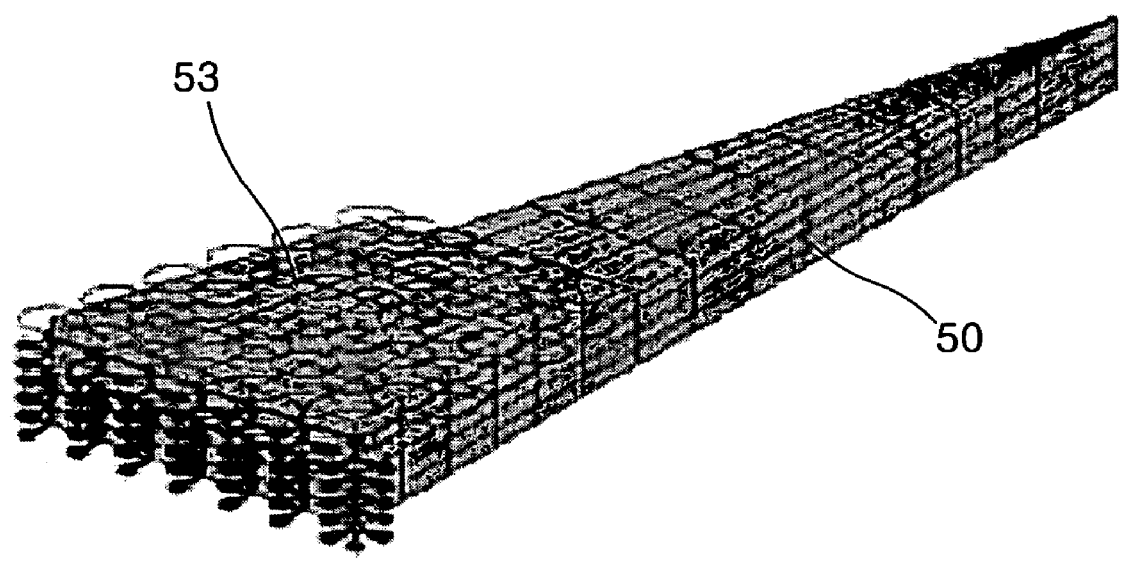
FIG. 6 is a view of a finite element model of a cantilever deposited with a piezoelectric element employed to a micro mass measuring apparatus according to an embodiment of the present invention.

In a numerical analysis, Q factor of 1000 and input voltage of 200 mN are inputted. FIG. 6 shows a finite element model for a numerical analysis, illustrating the triangular cantilever 50 deposited with the piezoelectric element 53. The piezoelectric element may be deposited on an area of the cantilever as large as possible. Since output current from the piezoelectric element is most affected by the size of the piezoelectric element, it is preferable that the piezoelectric element is formed as large as possible to effectively measure the resonance frequency according to the variation of the micro mass. For example, the piezoelectric element 53 may be formed in a trapezoid-shape.

Figure 7A:
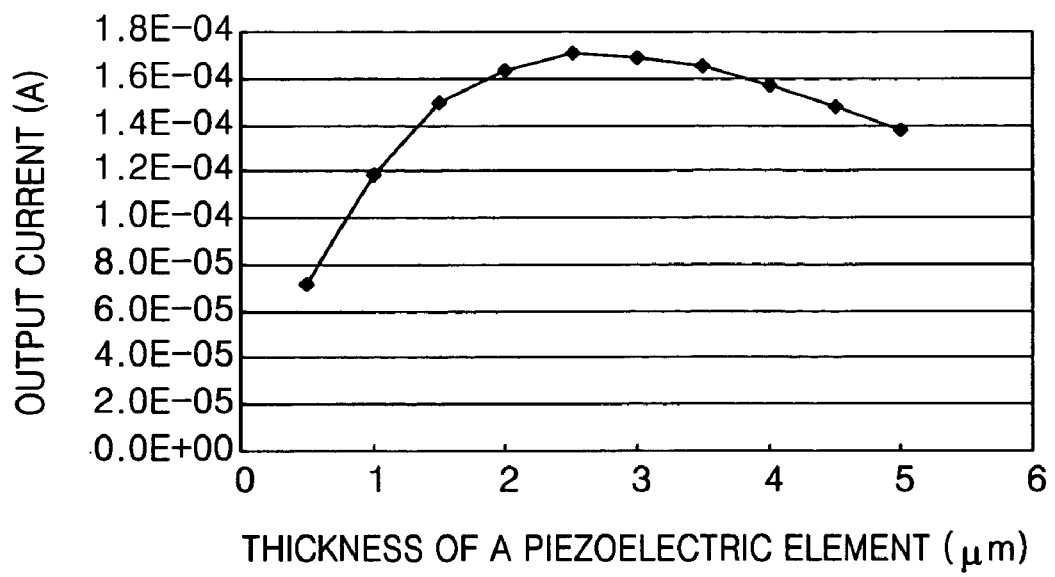
FIG. 7A is a graph illustrating output current with respect to a thickness of a piezoelectric element employed to a micro mass measuring apparatus according to an embodiment of the present invention.

To identify the affection of a thickness of the piezoelectric on the output current, the thickness t1 (see FIG. 3) is gradually varied in a state where a length L1 is 30 μm. FIG. 7A shows a graph illustrating the variation of the output current according to the thickness of the piezoelectric element 53. As shown in the graph, when the thickness t1 is 2.5 μm, the largest amount of output current is obtained.

Figure 7B:
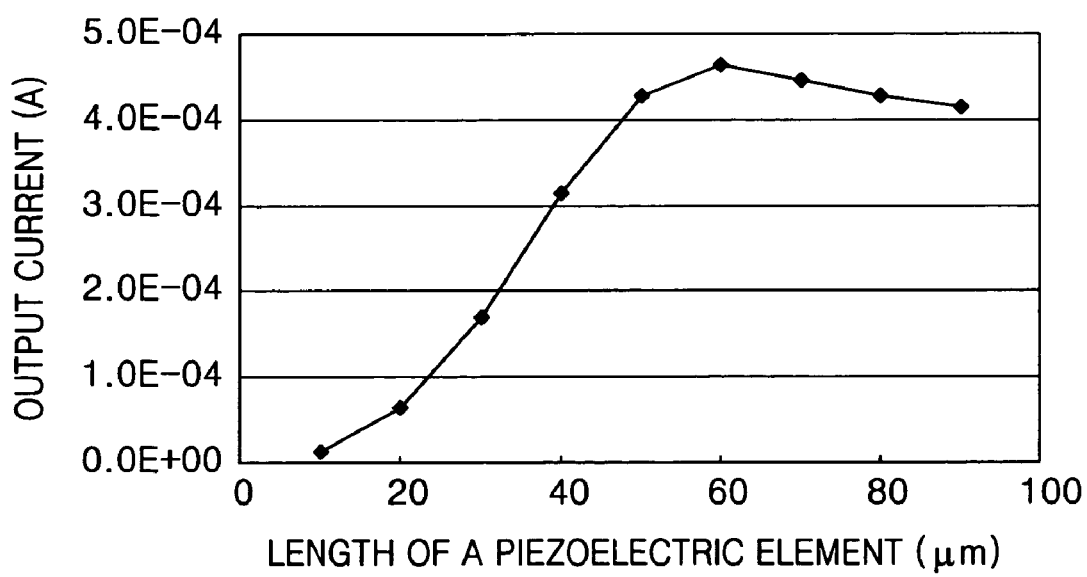
FIG. 7B is a graph illustrating output current with respect to a length of a piezoelectric element employed to a micro mass measuring apparatus according to an embodiment of the present invention.

To identify the variation of the output current according to the length L1 of the piezoelectric element, the output current is measured while increasing the length of the piezoelectric element 53 in a state where the thickness t1 is 2.5 μm. The result is shown in FIG. 7B. As shown in the graph, when the length L of the piezoelectric element is increased up to 60 μm, the output current is monotonically increased. When the length L is increased above 60 μm, the output current is gently reduced. According to a numeral analysis based on the result, it is preferable that a thickness of the piezoelectric element is 40-60% of that of the cantilever and a length thereof is 50-60% of that of the cantilever. That is, the thickness ratio and the length ratio between the piezoelectric element and the cantilever can be determined based on a case where a property of the micro cantilever manufactured through the MEMS process is similar to the numerical analysis result and the mathematical piezoelectric model.

Figure 9:
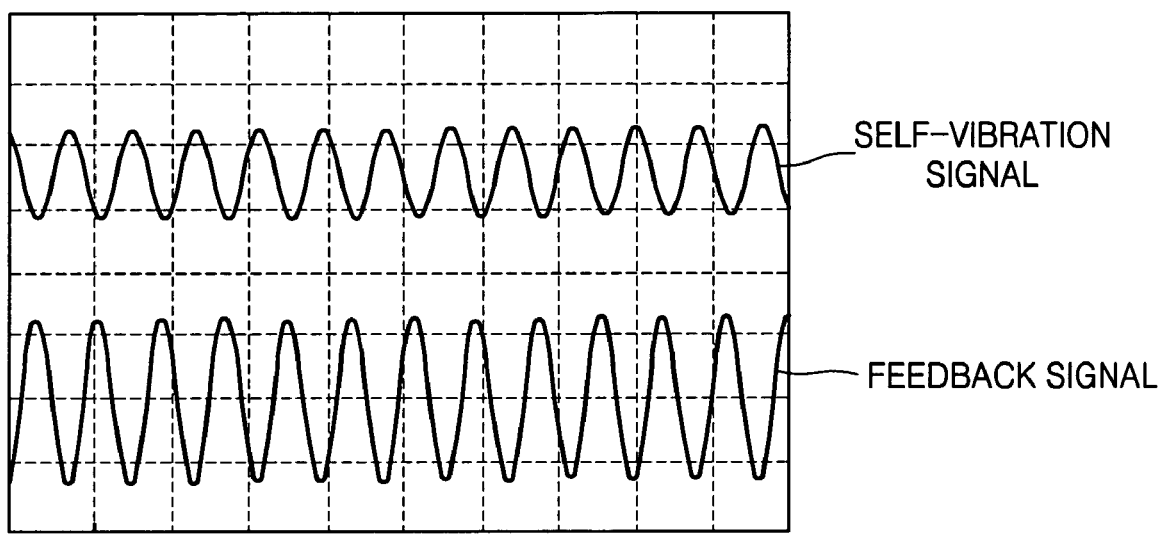
FIG. 9 is a graph illustrating a self-vibration signal and a feedback signal that are generated by an oscillation circuit applied to a micro mass measuring apparatus according to an embodiment of the present invention.

FIG. 8 shows the micro cantilever manufactured through the MEMS process and FIG. 9 shows graph illustrating signals outputted from the oscillation circuit through the oscilloscope.

In FIG. 9, a lower wave signal is a feedback vibration signal of the micro cantilever, which is returned to the cantilever through the oscillation circuit. An upper wave signal is a feedback signal outputted through the micro cantilever. That is, the upper wave signal shows a self-vibration signal representing that the cantilever continuously self-vibrates with the first resonance frequency.

As described above, the micro mass measuring apparatus of the present invention is designed such that the self-vibration of the cantilever and the measurement of subject mass can be simultaneously realized by the piezoelectric element applied with the oscillation circuit. Accordingly, an external driver such as a function generator is not required in the present invention.

The more concrete measuring example will be described hereinafter.

To measure the micro mass, it is preferable that a possibly large amount of the protein (the subject) is attached on the cantilever. To attach the protein on the cantilever as much as possible, sea mussel protein having high adhesive strength is used. An end of the micro cantilever 50 is stained with an aqueous solution containing the subject (the sea mussel protein). The oscillation circuit is connected to the cantilever 50 to measure the variation of the frequency. At this point, the first resonance frequency measured by the frequency measuring device 65 is 1.238544 MHz. The variation of the resonance frequency by the sea mussel protein is 85 Hz. The mass of the sea mussel protein calculated using Formula 15 representing the sensitiveness is $0.179483 \times 10^{-12}$ (g).

In the method for measuring the micro mass, the oscillation circuit 60 self-vibrates the cantilever 50 at the first resonance frequency. After the subject p is disposed on the cantilever 50, the cantilever 50 is further self-vibrated with the first varied resonance frequency and the mass of the subject p is measured using the varied resonance frequency.

When there is no subject p on the cantilever, the oscillation circuit 60 continuously excites the cantilever through the piezoelectric element 53 and the first resonance frequency of the cantilever is measured.

After the subject p is reattached on the cantilever 50, the resonance frequency varied by the subject P is measured to measure the variation of the resonance frequency. The mass of the subject P is measured using Formula 15 according to the variation of the resonance frequency. As described above, the cantilever is actively driven by the oscillation circuit and the mass of the subject can be measured according to the resonance frequency variation by the subject p without using a separated measuring device.

According to the above described micro mass measuring apparatus and method, since the self driving of the cantilever and the measuring of the resonance frequency are simultaneously realized by the single piezoelectric element, a separated vibrator and a separated resonance frequency measuring device are not required. Accordingly, the structure of the micro mass measuring apparatus can be simplified. In addition, the micro cantilever may be manufactured through the MEMS process. In addition, when an arrangement having a plurality of cantilevers is designed, mass of a variety of bio subjects can be measured simultaneously. Therefore, when the micro cantilever is applied to the LOC, it becomes possible to realize a portable DNA or protein detector.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A micro mass measuring apparatus comprising:
    a cantilever on which a subject is attached, wherein the cantilever comprises a shape ratio determined by sensitiveness and a separation factor and is applied to a lab-on-a-chip;
    a piezoelectric element formed on the cantilever;
    an oscillation circuit comprising an amplifier for amplifying an output signal from the cantilever; and a feedback for inputting the amplified signal to the cantilever, the oscillation circuit for actively vibrating the cantilever and providing a varied resonance frequency by the subject; and
    a frequency measuring device for measuring a resonance frequency of the cantilever.

2. The micro mass measuring apparatus of claim 1, wherein the separation factor is defined by a value obtained by dividing a difference between a first resonance frequency of the cantilever and a second resonance frequency varied by the subject by the first resonance frequency.

3. The micro mass measuring apparatus of claim 1, wherein the cantilever is formed in a triangular-shape.

4. The micro mass measuring apparatus of claim 3, wherein a ratio between a length, width and thickness of the cantilever is in a range of 20:6:1-20:18:1.

5. The micro mass measuring apparatus of claim 1, wherein an area of the cantilever, on which the subject is attached, is $1/15$-$1/10$ of an entire area of the cantilever.

6. The micro mass measuring apparatus of claim 1, wherein a thickness of the piezoelectric element is about 40-60% of a thickness of the cantilever.

7. The micro mass measuring apparatus of claim 1, wherein a length of the piezoelectric element is about 50-60% of a length of the cantilever.

8. A method for measuring micro mass using a mass micro-balancing technology, comprising:
    self-vibrating a cantilever comprising a shape ratio determined by sensitiveness and a separation factor, the cantilever applied to a lab-on-a-chip through a piezoelectric element using an oscillation circuit comprising an amplifier for amplifying an output signal from the cantilever; and a feedback for inputting the amplified signal to the cantilever, the oscillation circuit at a first resonance frequency;
    attaching a subject on the cantilever and self-vibrating the cantilever with a first resonance frequency varied by the subject; and
    measuring mass of the subject using resonance frequencies variation due to the subject.

9. The method as in claim 8, wherein the first resonance frequency provides for determination of a mass of the cantilever.

10. The method as in claim 8, wherein a second resonance frequency is separated from the first resonance frequency.

11. The method as in claim 8, wherein the measuring is performed in a liquid.

12. The method as in claim 11, wherein the measuring comprises accounting for effects of the liquid.

13. A micro mass measuring apparatus comprising:
    a cantilever comprising a shape ratio determined by sensitiveness and a separation factor, the cantilever applied to a lab-on-a-chip onto which a subject is attached;
    a single piezoelectric element formed on the cantilever and comprising an oscillation circuit for actively vibrating the cantilever and measuring a resonance frequency of the cantilever; wherein measurement of the resonance frequency provides for determining the mass.

* * * * *